US008200322B2

(12) United States Patent
Ousdigian et al.

(10) Patent No.: US 8,200,322 B2
(45) Date of Patent: Jun. 12, 2012

(54) ELECTROGRAM STORAGE FOR SUSPECTED NON-PHYSIOLOGICAL EPISODES

(75) Inventors: Kevin T. Ousdigian, St. Paul, MN (US); Catherine R. Condie, Shoreview, MN (US); Karen J. Kleckner, New Brighton, MN (US); Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 937 days.

(21) Appl. No.: 12/182,687

(22) Filed: Jul. 30, 2008

(65) Prior Publication Data
US 2009/0299422 A1 Dec. 3, 2009

Related U.S. Application Data

(60) Provisional application No. 61/130,794, filed on Jun. 2, 2008.

(51) Int. Cl.
*A61B 5/0468* (2006.01)
(52) U.S. Cl. ...................................... 600/518
(58) Field of Classification Search .............. 607/8, 28; 600/515, 518
See application file for complete search history.

(56) References Cited

U.S. PATENT DOCUMENTS

| 4,140,131 A | 2/1979 | Dutcher et al. |
| 4,374,382 A | 2/1983 | Markowitz |
| 4,428,378 A | 1/1984 | Anderson et al. |
| 4,549,548 A | 10/1985 | Wittkampf et al. |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,137,021 A | 8/1992 | Wayne et al. |

(Continued)

FOREIGN PATENT DOCUMENTS
GB 2362216 A 11/2001
(Continued)

OTHER PUBLICATIONS

U.S. Appl. No. 61/058,153 by Stadler et al., entitled "Impedance Variability Analysis to Identify Lead-Related Conditions" filed Jun. 2, 2008.

(Continued)

*Primary Examiner* — Scott Getzow
*Assistant Examiner* — Amanda Patton
(74) *Attorney, Agent, or Firm* — Michael C. Soldner

(57) ABSTRACT

Techniques for storing electrograms (EGMS) that are associated with sensed episodes or events that may be non-physiological and, instead, associated with a sensing integrity condition are described. In some examples, a device or system identifies suspected non-physiological NSTs, and stores an EGM for the suspected non-physiological NSTs within an episode log. In some examples, a device or system determines whether to store an EGM for a suspected non-physiological episode or event based on whether an impedance integrity criterion has been satisfied. For example, a device or system may store an EGM for a detected short interval if the impedance integrity criterion has been met. In some examples, a device or system determines whether to buffer EGM data based on whether an impedance integrity criterion or other sensing integrity criterion has been met.

18 Claims, 11 Drawing Sheets

U.S. PATENT DOCUMENTS

| | | | |
|---|---|---|---|
| 5,168,871 A | 12/1992 | Grevious | |
| 5,184,614 A | 2/1993 | Collins et al. | |
| 5,193,535 A | 3/1993 | Bardy et al. | |
| 5,201,865 A | 4/1993 | Kuehn | |
| 5,215,081 A | 6/1993 | Ostroff | |
| 5,224,475 A | 7/1993 | Berg et al. | |
| 5,226,415 A | 7/1993 | Girodo et al. | |
| 5,292,343 A | 3/1994 | Blanchette et al. | |
| 5,312,441 A | 5/1994 | Mader et al. | |
| 5,314,450 A | 5/1994 | Thompson | |
| 5,324,315 A | 6/1994 | Grevious | |
| 5,354,319 A | 10/1994 | Wyborny et al. | |
| 5,381,803 A | 1/1995 | Herleikson et al. | |
| 5,383,909 A | 1/1995 | Keimel | |
| 5,411,530 A | 5/1995 | Akhtar | |
| 5,431,692 A | 7/1995 | Hansen et al. | |
| 5,462,060 A | 10/1995 | Jacobson et al. | |
| 5,507,746 A | 4/1996 | Lin | |
| 5,507,786 A | 4/1996 | Morgan et al. | |
| 5,534,018 A | 7/1996 | Wahlstrand et al. | |
| 5,545,183 A | 8/1996 | Altman | |
| 5,545,186 A | 8/1996 | Olson et al. | |
| 5,549,646 A | 8/1996 | Katz et al. | |
| 5,558,098 A | 9/1996 | Fain | |
| 5,564,434 A | 10/1996 | Halperin et al. | |
| 5,660,183 A | 8/1997 | Chiang et al. | |
| 5,707,398 A | 1/1998 | Lu | |
| 5,722,997 A | 3/1998 | Nedungadi et al. | |
| 5,730,141 A | 3/1998 | Fain et al. | |
| 5,741,311 A | 4/1998 | Mc Venes et al. | |
| 5,755,735 A | 5/1998 | Richter et al. | |
| 5,755,736 A | 5/1998 | Gillberg et al. | |
| 5,755,742 A | 5/1998 | Schuelke et al. | |
| 5,776,168 A | 7/1998 | Gunderson | |
| 5,814,088 A | 9/1998 | Paul et al. | |
| 5,868,793 A | 2/1999 | Nitzsche et al. | |
| 5,891,170 A | 4/1999 | Nitzsche et al. | |
| 5,891,179 A | 4/1999 | Er et al. | |
| 5,897,577 A | 4/1999 | Cinbis et al. | |
| 5,910,156 A | 6/1999 | Cinbis et al. | |
| 5,944,746 A | 8/1999 | Kroll | |
| 6,067,473 A | 5/2000 | Greeninger et al. | |
| 6,070,097 A | 5/2000 | Kreger et al. | |
| 6,085,118 A | 7/2000 | Hirschberg et al. | |
| 6,112,119 A | 8/2000 | Schuelke et al. | |
| 6,129,746 A | 10/2000 | Levine et al. | |
| 6,141,585 A | 10/2000 | Prutchi et al. | |
| 6,155,267 A | 12/2000 | Nelson | |
| 6,169,923 B1 | 1/2001 | Kroll | |
| 6,266,554 B1 | 7/2001 | Hsu et al. | |
| 6,317,632 B1 | 11/2001 | Krig et al. | |
| 6,317,633 B1 | 11/2001 | Jorgenson et al. | |
| 6,393,316 B1 | 5/2002 | Gillberg et al. | |
| 6,434,428 B1 | 8/2002 | Sloman et al. | |
| 6,445,952 B1 | 9/2002 | Manrodt et al. | |
| 6,477,417 B1 | 11/2002 | Levine | |
| 6,493,586 B1 | 12/2002 | Stahmann et al. | |
| 6,629,931 B1 | 10/2003 | Begemann et al. | |
| 6,650,931 B1 | 11/2003 | McClure et al. | |
| 6,658,294 B1 | 12/2003 | Zadeh et al. | |
| 6,721,600 B2 | 4/2004 | Jorgenson et al. | |
| 6,760,624 B2 | 7/2004 | Anderson et al. | |
| 6,788,971 B1 | 9/2004 | Sloman et al. | |
| 6,865,141 B2 | 3/2005 | Tada et al. | |
| 7,047,083 B2 | 5/2006 | Gunderson et al. | |
| 7,167,747 B2 | 1/2007 | Gunderson et al. | |
| 7,236,828 B2 | 6/2007 | Casavant et al. | |
| 7,266,409 B2 | 9/2007 | Gunderson | |
| 7,289,851 B2 | 10/2007 | Gunderson et al. | |
| 7,333,855 B2 | 2/2008 | Gunderson et al. | |
| 7,369,893 B2 | 5/2008 | Gunderson | |
| 7,539,540 B2 | 5/2009 | Gunderson et al. | |
| 7,567,835 B2 | 7/2009 | Gunderson et al. | |
| 2001/0031997 A1 | 10/2001 | Lee | |
| 2001/0037366 A1 | 11/2001 | Webb et al. | |
| 2002/0091333 A1 | 7/2002 | Hsu et al. | |
| 2002/0116031 A1 | 8/2002 | Vonk | |
| 2002/0118215 A1 | 8/2002 | Ball et al. | |
| 2002/0120307 A1 | 8/2002 | Jorgenson et al. | |
| 2003/0074026 A1 | 4/2003 | Thompson et al. | |
| 2003/0204215 A1 | 10/2003 | Gunderson et al. | |
| 2004/0015197 A1 | 1/2004 | Gunderson | |
| 2004/0088018 A1 | 5/2004 | Sawchuk et al. | |
| 2004/0106955 A1 | 6/2004 | Swerdlow et al. | |
| 2004/0122487 A1 | 6/2004 | Hatlestad et al. | |
| 2004/0162593 A1 | 8/2004 | Jorgenson et al. | |
| 2004/0186388 A1 | 9/2004 | Gerasimov | |
| 2004/0215270 A1 | 10/2004 | Ritscher et al. | |
| 2004/0220631 A1 | 11/2004 | Burnes et al. | |
| 2004/0230233 A1 | 11/2004 | Gunderson et al. | |
| 2004/0230242 A1 | 11/2004 | van Dam et al. | |
| 2005/0137636 A1* | 6/2005 | Gunderson et al. | 607/27 |
| 2005/0154421 A1 | 7/2005 | Ousdigian | |
| 2005/0159785 A1 | 7/2005 | Rueter | |
| 2006/0074454 A1 | 4/2006 | Freeberg | |
| 2006/0116733 A1 | 6/2006 | Gunderson | |
| 2006/0235476 A1 | 10/2006 | Gunderson et al. | |
| 2008/0082012 A1 | 4/2008 | Gunderson et al. | |
| 2008/0161872 A1 | 7/2008 | Gunderson | |
| 2010/0058462 A1 | 3/2010 | Chow | |

FOREIGN PATENT DOCUMENTS

| | | |
|---|---|---|
| WO | 8901803 A1 | 3/1989 |
| WO | WO 97/35516 A1 | 10/1997 |
| WO | WO 97/36647 A1 | 10/1997 |
| WO | WO 02/24276 A1 | 3/2002 |
| WO | WO 2005/056109 A1 | 6/2005 |
| WO | 2006050360 A1 | 5/2006 |
| WO | WO 2006/116430 A2 | 11/2006 |

OTHER PUBLICATIONS

Response to Written Opinion from corresponding PCT Application Serial No. PCT/US2008/009199 filed on Apr. 2, 2010 (15 pages).
U.S. Appl. No. 12/695,811, filed Jan. 28, 2010 entitled "Storage of Data for Evaluation of Lead Integrity" by Hoeppner et al.
Invitation to Pay Additional Fees and, Where Applicable, Protest Fee from corresponding PCT Application Serial No. PCT/US2008/009199 mailed Apr. 8, 2009 (4 pages).
International Search Report and Written Opinion from corresponding PCT Application Serial No. PCT/US2008/009199 mailed Jun. 29, 2009 (17 pages).
International Preliminary Report on Patentability from corresponding PCT Application Serial No. PCT/US2008/009199 dated Aug. 20, 2010 (13 pages).

* cited by examiner

ELECTROGRAM STORAGE FOR SUSPECTED NON-PHYSIOLOGICAL EPISODES

This application claims the benefit of U.S. Provisional Application No. 61/130,794, filed Jun. 2, 2008, the entire content of which is incorporated herein by reference.

TECHNICAL FIELD

The disclosure relates to implantable medical devices, and, more particularly, to collection of diagnostic information by implantable medical devices.

BACKGROUND

A variety of implantable medical devices for delivering a therapy and/or monitoring a physiological condition have been clinically implanted or proposed for clinical implantation in patients. Some implantable medical devices may employ one or more elongated electrical leads carrying stimulation electrodes, sense electrodes, and/or other sensors. Implantable medical devices may deliver electrical stimulation or fluid therapy to, and/or monitor conditions associated with, the heart, muscle, nerve, brain, stomach or other organs or tissue. Implantable medical leads may be configured to allow electrodes or other sensors to be positioned at desired locations for delivery of stimulation or sensing. For example, electrodes or sensors may be carried at a distal portion of a lead. A proximal portion of the lead may be coupled to an implantable medical device housing, which may contain circuitry such as signal generation and/or sensing circuitry.

Some implantable medical devices, such as cardiac pacemakers or implantable cardioverter-defibrillators, provide therapeutic electrical stimulation to the heart via electrodes carried by one or more implantable leads. The electrical stimulation may include signals such as pulses or shocks for pacing, cardioversion or defibrillation. In some cases, an implantable medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

Leads associated with an implantable medical device typically include a lead body containing one or more elongated electrical conductors that extend through the lead body from a connector assembly provided at a proximal lead end to one or more electrodes located at the distal lead end or elsewhere along the length of the lead body. The conductors connect stimulation and/or sensing circuitry within an associated implantable medical device housing to respective electrodes or sensors. Some electrodes may be used for both stimulation and sensing. Each electrical conductor is typically electrically isolated from other electrical conductors, and is encased within an outer sheath that electrically insulates the lead conductors from body tissue and fluids.

Cardiac lead bodies tend to be continuously flexed by the beating of the heart. Other stresses may be applied to the lead body during implantation or lead repositioning. Patient movement can cause the route traversed by the lead body to be constricted or otherwise altered, causing stresses on the lead body. The electrical connection between implantable medical device connector elements and the lead connector elements can be intermittently or continuously disrupted. Connection mechanisms, such as set screws, may be insufficiently tightened at the time of implantation, followed by a gradual loosening of the connection. Also, lead pins may not be completely inserted. In some cases, changes in leads or connections may result in intermittent or continuous changes in lead impedance.

Short circuits, open circuits or significant changes in impedance may be referred to, in general, as lead related conditions. In the case of cardiac leads, sensing of an intrinsic heart rhythm through a lead can be altered by lead related conditions. Structural modifications to leads, conductors or electrodes may alter sensing integrity. Furthermore, impedance changes in the stimulation path due to lead related conditions may affect sensing and stimulation integrity for pacing, cardioversion, or defibrillation. In addition to lead related conditions, conditions associated with sensor devices or sensing circuitry, as well as conditions associated with electrodes or sensors not located on leads, may affect sensing integrity. Furthermore, T-wave oversensing, where the implantable medical device misidentifies T-waves as P-waves or R-waves, oversensing due to ambient radiofrequency noise, oversensing due to patient movement artifacts, or other over or undersensing issues, which may be unrelated to the integrity of implantable leads or other medical device components, may affect sensing integrity.

SUMMARY

In general, the disclosure is directed to techniques for storing electrograms (EGMs) that are associated with sensed episodes or events that may be non-physiological and, instead, associated with a sensing integrity condition. The storage of such EGMs may facilitate evaluation of the EGMs to determine whether a sensing integrity condition is present in an implantable medical device (IMD) system. The EGMs may be considered in conjunction within other sensing integrity data, such as lead impedance data.

Some IMDs store cardiac EGMs for physiological episodes, such as tachyarrhythmias, within an episode log. For example, some IMDs store cardiac EGMs for atrial and ventricular tachycardia and fibrillation episodes in response to the detection of the tachycardia or fibrillation. The EGM may include data collected by the IMD during detection of the tachyarrhythmia, as well as after detection, e.g., during treatment of the tachyarrhythmia. The data stored for the episode may also include a marker channel associated with the EGM. The marker channel may annotate the EGM with events detected by the IMD, such as ventricular or atrial depolarizations, as well an indication of when during the episode a responsive therapy was delivered by the IMD.

Some IMDs also store EGMs and marker channels for non-sustained tachyarrhythmias (NSTs), which may comprise a series of rapid ventricular or atrial depolarizations that did not meet the criterion for classification as a tachycardia or fibrillation. An NST may fail to meet the criterion for classification as a tachycardia or fibrillation if, for example, the episode was too short to meet a number of intervals to detect (NID) threshold for tachycardia or fibrillation.

In some examples according to this disclosure, a device or system identifies suspected non-physiological NSTs, and stores an EGM for the suspected non-physiological NSTs within an episode log. The EGM may be stored with a marker channel. A suspected non-physiological NST may be identified based on, for example, the rate of sensed cardiac events, e.g. depolarizations, during the NST. A cardiac event rate above a threshold may be more likely the result of a sensing integrity condition, e.g., the device misidentifying noise as depolarizations, than an actual tachyarrhythmia. In some examples, a device or system additionally or alternatively identifies a suspected non-physiological NST based on a morphological analysis of the EGM for the NST, which may distinguish between noise and cardiac depolarizations.

In some examples, a device or system additionally or alternatively identifies a suspected non-physiological NST based on the presence or absence of a confirmatory indication of tachyarrhythmia from one or more other sensing channels or sensors. Another sensing channel may include a different sensing electrode configuration than the primary sensing channel that detected the NST and/or different signal processing circuitry. A different sensing electrode configuration may include one or more electrodes that are different than the electrodes of the primary sensing electrode configuration that detected the NST. Other sensors may include, as examples, a cardiovascular, e.g., intracardiac, pressure sensor, a motion sensor, e.g., an accelerometer or piezoelectric element, or a heart sound sensor. Mechanical activity (e.g., contraction) of the heart may be detected based on the signals provided by these or other sensors, and a device or system according to the invention may determine whether detected cardiac depolarizations are correlated with mechanical activity of the heart in order to determine whether an NST is suspected of being non-physiological.

In some examples, a device or system determines whether to store an EGM for a suspected non-physiological episode or event based on whether an impedance integrity criterion has been satisfied. The impedance integrity criterion may be satisfied based on one or more impedance measurements. The impedance measurements may be of one or more electrical paths. Each electrical path includes a plurality of electrodes, one or more of which may be located on an implantable medical lead. An electrical path for which impedance is measured may include the electrodes used to sense cardiac electrical signals.

The impedance integrity criterion may indicate a possible sensing integrity condition, which may be a lead related condition, such as a lead fracture or short. Based on satisfaction of the impedance integrity criterion, a device or system may provide alerts, or take other actions. Based on satisfaction of the impedance integrity criterion, a device or system may also store EGMs for subsequent suspected non-physiological episodes or events.

For example, a device or system may store an EGM for a detected short interval if the impedance integrity criterion has been met. A short interval may be an interval between consecutive sensed cardiac events, e.g., depolarizations, that is less than a threshold. An interval shorter than the threshold may indicate a sensing integrity condition, e.g., that the device or system has misidentified noise as a depolarization for one or both of the sensed depolarizations.

A device or system in some examples may suspend storage of EGMs for short intervals when a suspected non-physiological NST is detected. An EGM for a suspected non-physiological NST may be more probative of sensing integrity conditions than an EGM for a short interval. A device or system according to some examples may suspend storage of EGMs for short intervals when a suspected non-physiological NST is detected to conserve memory resources and ensure that EGMs for suspected non-physiological NSTs are retained in the memory.

In some examples, a device or system may buffer EGM data to enable storing a period of the EGM that preceded detection of a suspected non-physiological NST or short interval. However, buffering EGM data may consume memory or other resources of the device or system. In some examples, a device or system determines whether to buffer EGM data based on whether an impedance integrity criterion or other sensing integrity criterion has been met. In other words, in some examples, a device begins buffering EGM data when an impedance integrity criterion or other sensing integrity criteria has been met. Other sensing integrity criteria may include detecting a threshold number of non-physiological NSTs, detecting a threshold number of short intervals, or detecting both a threshold number of non-physiological NSTs and a threshold number of short intervals.

In one example, the disclosure provides a method comprising receiving a cardiac electrical signal, detecting a suspected non-physiological non-sustained tachyarrhythmia based on the cardiac electrical signal, and storing an electrogram for the suspected non-physiological non-sustained tachyarrhythmia based on the detection, the electrogram including at least a portion of the cardiac electrical signal.

In another example, the disclosure provides a system comprising a memory, a plurality of electrodes, an electrical sensing module that receives a cardiac electrical signal from the plurality of electrodes, a non-physiological non-sustained tachyarrhythmia detection module that detects a suspected non-physiological non-sustained tachyarrhythmia based on the cardiac electrical signal, and an episode storage evaluation module that controls storage of an electrogram for the suspected non-physiological non-sustained tachyarrhythmia within the memory based on the detection, the electrogram including at least a portion of the cardiac electrical signal.

In another example, the disclosure provides a system comprising means for receiving a cardiac electrical signal, means for detecting a suspected non-physiological non-sustained tachyarrhythmia based on the cardiac electrical signal, and means for storing an electrogram for the suspected non-physiological non-sustained tachyarrhythmia based on the detection, the electrogram including at least a portion of the cardiac electrical signal.

In another example, the disclosure provides a computer readable medium comprising instructions that cause a processor to detect a suspected non-physiological non-sustained tachyarrhythmia based on a cardiac electrical signal, and control storage of an electrogram for the suspected non-physiological non-sustained tachyarrhythmia based on the detection, the electrogram including at least a portion of the cardiac electrical signal.

In another example, the disclosure provides a system comprising a memory, a plurality of electrodes, an electrical sensing module that receives a cardiac electrical signal from the plurality of electrodes and measures an impedance of an electrical path comprising the electrodes, and a processor that compares an interval between the events to a threshold, and determines whether to store an electrogram for the interval within the memory based on the comparison and the impedance measurement, the electrogram including at least a portion of the cardiac electrical signal.

In another example, the disclosure provides a system comprising a memory, a plurality of electrodes, an electrical sensing module that receives a cardiac electrical signal from the plurality of electrodes, and a processor that determines whether a sensing integrity criterion is met, and buffers the cardiac electrical signal for storage of an electrogram based on the determination.

DETAILED DESCRIPTION

Figure 1:
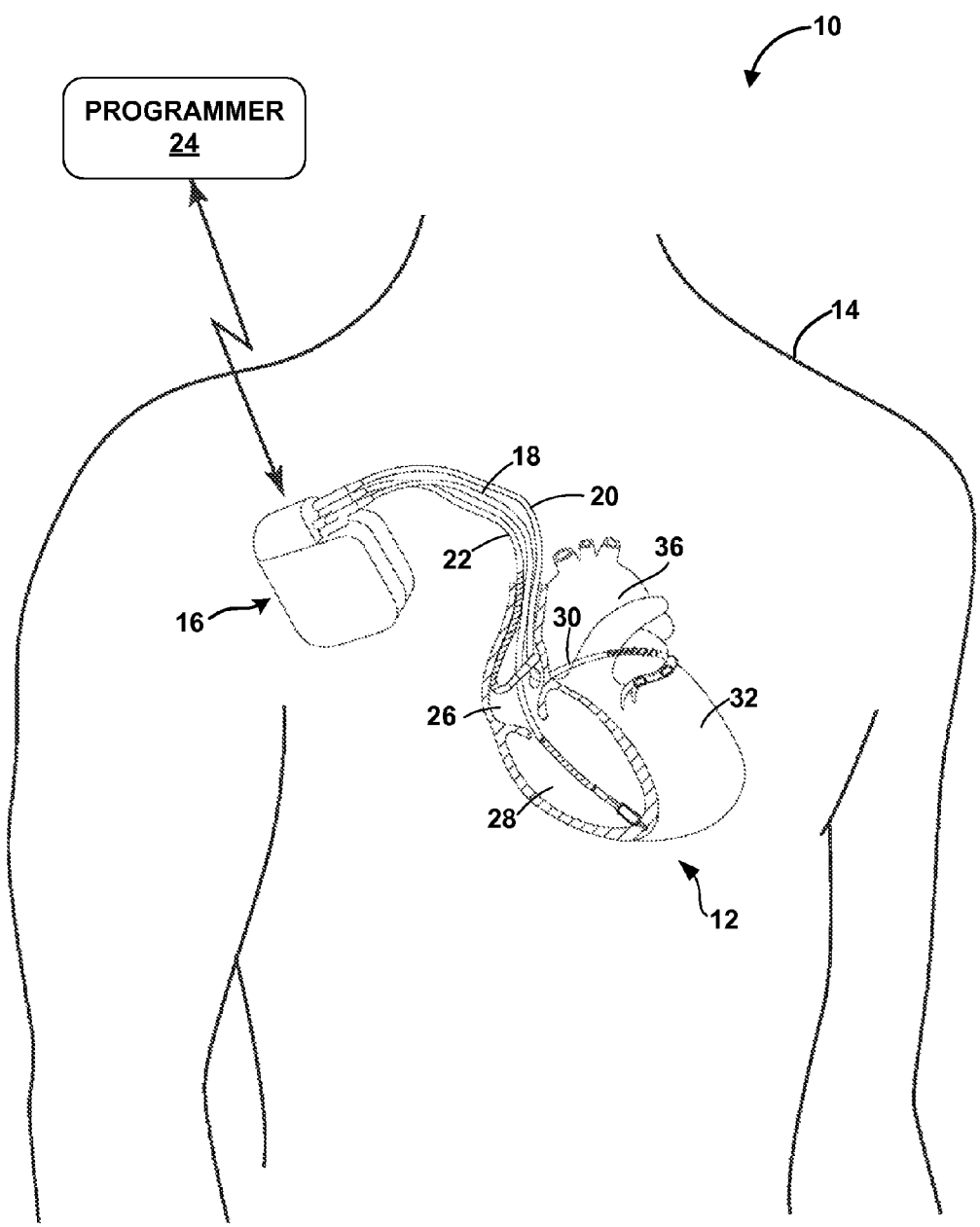
FIG. 1 is a conceptual diagram illustrating an example therapy system comprising an implantable medical device (IMD) for delivering stimulation therapy to a heart of a patient via implantable leads.

FIG. 1 is a conceptual diagram illustrating an example therapy system 10 that may be used to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 12 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into right atrium 26 of heart 12. In some alternative embodiments, therapy system 10 may include an additional lead or lead segment (not shown in FIG. 1) that deploys one or more electrodes within the vena cava or other vein. These electrodes may allow alternative electrical sensing configurations that may provide improved sensing accuracy in some patients.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver cardioversion or defibrillation therapy to heart 12 in the form of electrical pulses. In some examples, IMD 16 may be programmed to deliver a progression of therapies, e.g., pulses with increasing energy levels, until a tachyarrhythmia of heart 12 is stopped. IMD 16 detects tachycardia or fibrillation employing one or more tachycardia or fibrillation detection techniques known in the art.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. It should be noted that the user may also interact with programmer 24 or IMD 16 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16.

The user may use programmer 24 to program a therapy progression, select electrodes used to deliver defibrillation pulses, select waveforms for the defibrillation pulses, or select or configure a fibrillation detection algorithm for IMD 16. The user may also use programmer 24 to program similar aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

IMD 16 is an example of a device that may store electrograms (EGMs) that are associated with sensed episodes or events that may be non-physiological and, instead, associated with a sensing integrity condition. Such EGMs may be retrieved from IMD 16 by programmer 24, and displayed by programmer 24 for evaluation by a clinician or other user to, for example, determine whether a sensing integrity condition is present in IMD 16, leads 18, 20 and 22, or any other components of system 10. The EGMs may be considered in conjunction within other sensing integrity data, such as lead impedance data, which may also be stored by IMD 16, and retrieved and displayed by programmer 24. The EGMs may be stored with respective marker channels.

In other examples, one or more devices other than IMD 16 may, alone, or in combination with IMD, implement the techniques described herein. For example, programmer 24 or another external device may store EGMs based on a cardiac signal received from IMD 16. Programmer 24 or another external device may determine whether to store the EGMs, according to any of the techniques described herein, based on the cardiac signal or other signals or information received from IMD 16. Furthermore, in some examples, the medical device and/or leads are not implanted.

Figure 2:
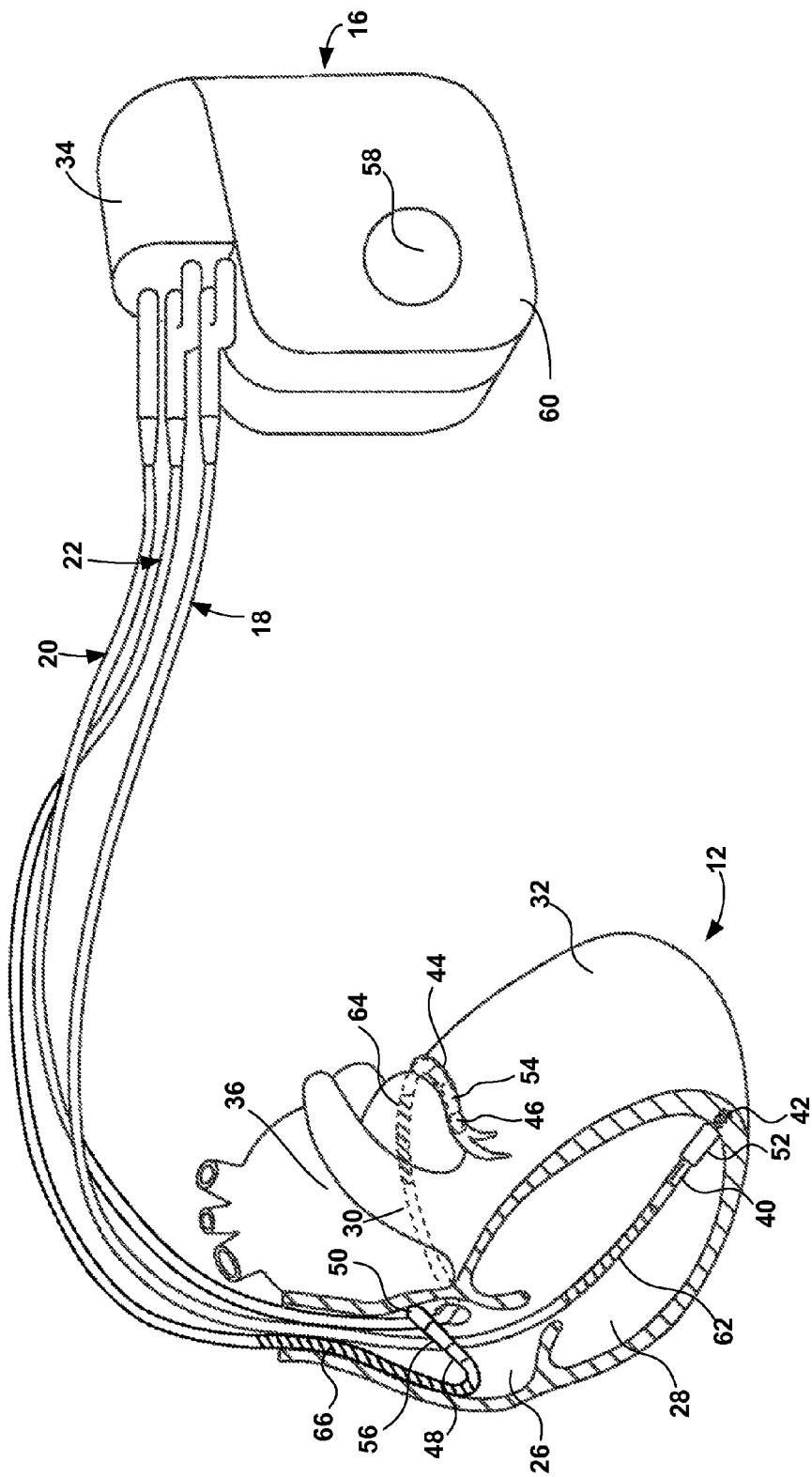
FIG. 2 is a conceptual diagram further illustrating the IMD and leads of the system of FIG. 1 in conjunction with the heart.

FIG. 2 is a conceptual diagram illustrating a three-lead IMD 16 and leads 18, 20 and 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36 in the illustrated example, but other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other embodiments, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor couple to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

Any multipolar combination of two or more of electrodes 40, 42, 44, 46, 48, 50, 58, 62, 64, and 66 may be considered a sensing electrode configuration. Usually, but not necessarily, a sensing electrode configuration is a bipolar electrode combination on the same lead, such as electrodes 40 and 42 of lead 18. On one lead having three electrodes, there may be at least three different sensing electrode configurations available to IMD 16. These sensing electrode configurations are, for the example of lead 18, tip electrode 42 and ring electrode 40, tip electrode 42 and elongated electrode 62, and ring electrode 40 and elongated electrode 62. However, some embodiments may utilize sensing electrode configurations having electrodes of two different leads. Further, a sensing electrode configuration may utilize housing electrode 58, which may provide a unipolar sensing electrode configuration. In some examples, a sensing electrode configuration may comprise multiple housing electrodes 58. In any sensing electrode configuration, the polarity of each electrode in the may be configured as appropriate for the application of the sensing electrode configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3.

Figure 3:
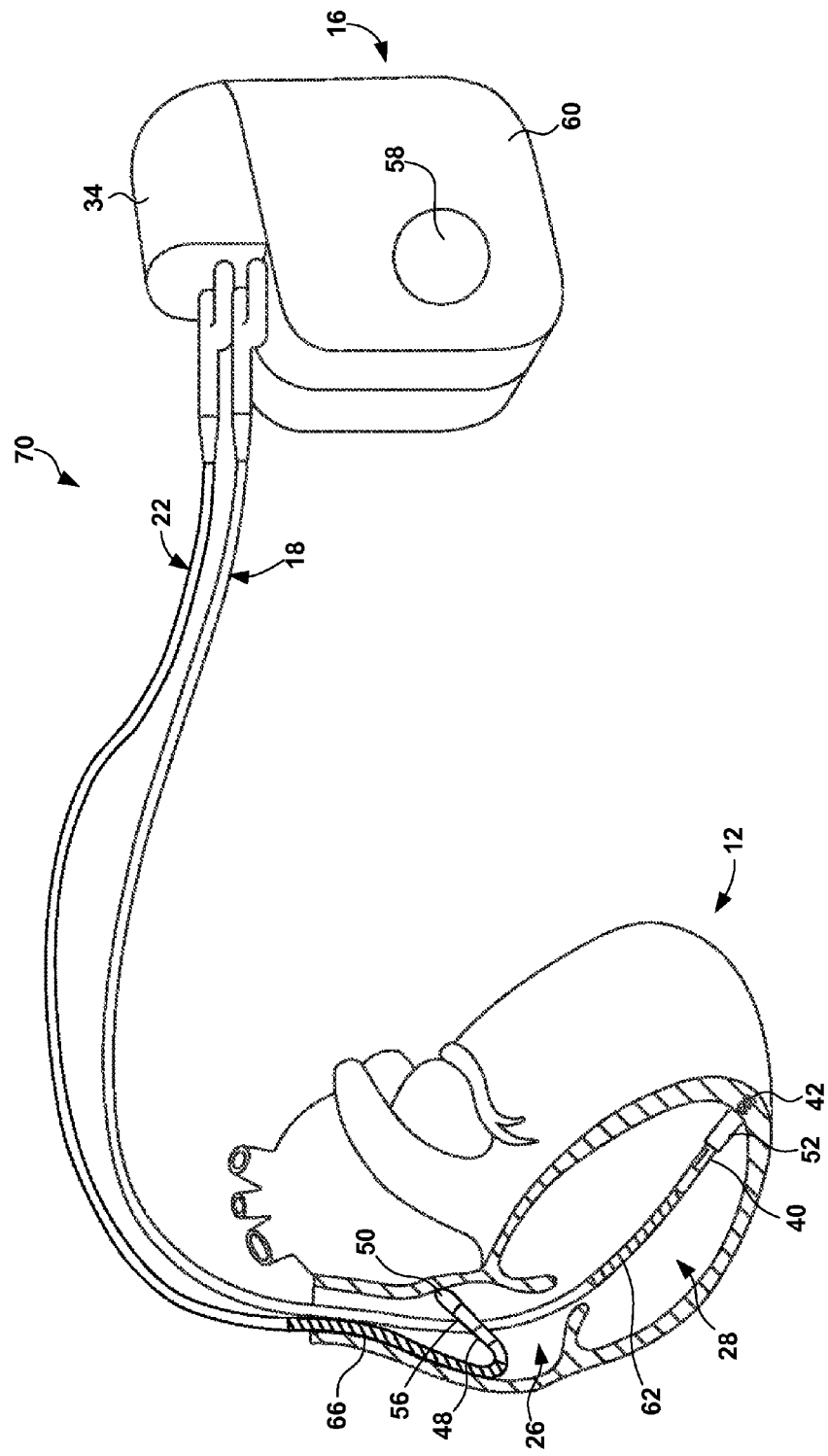
FIG. 3 is a conceptual diagram illustrating another example therapy system comprising the IMD of FIG. 1 coupled to a different configuration of leads.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12. Storage of EGMs according to the techniques described herein may also be performed by or with respect to system 70.

Figure 4:
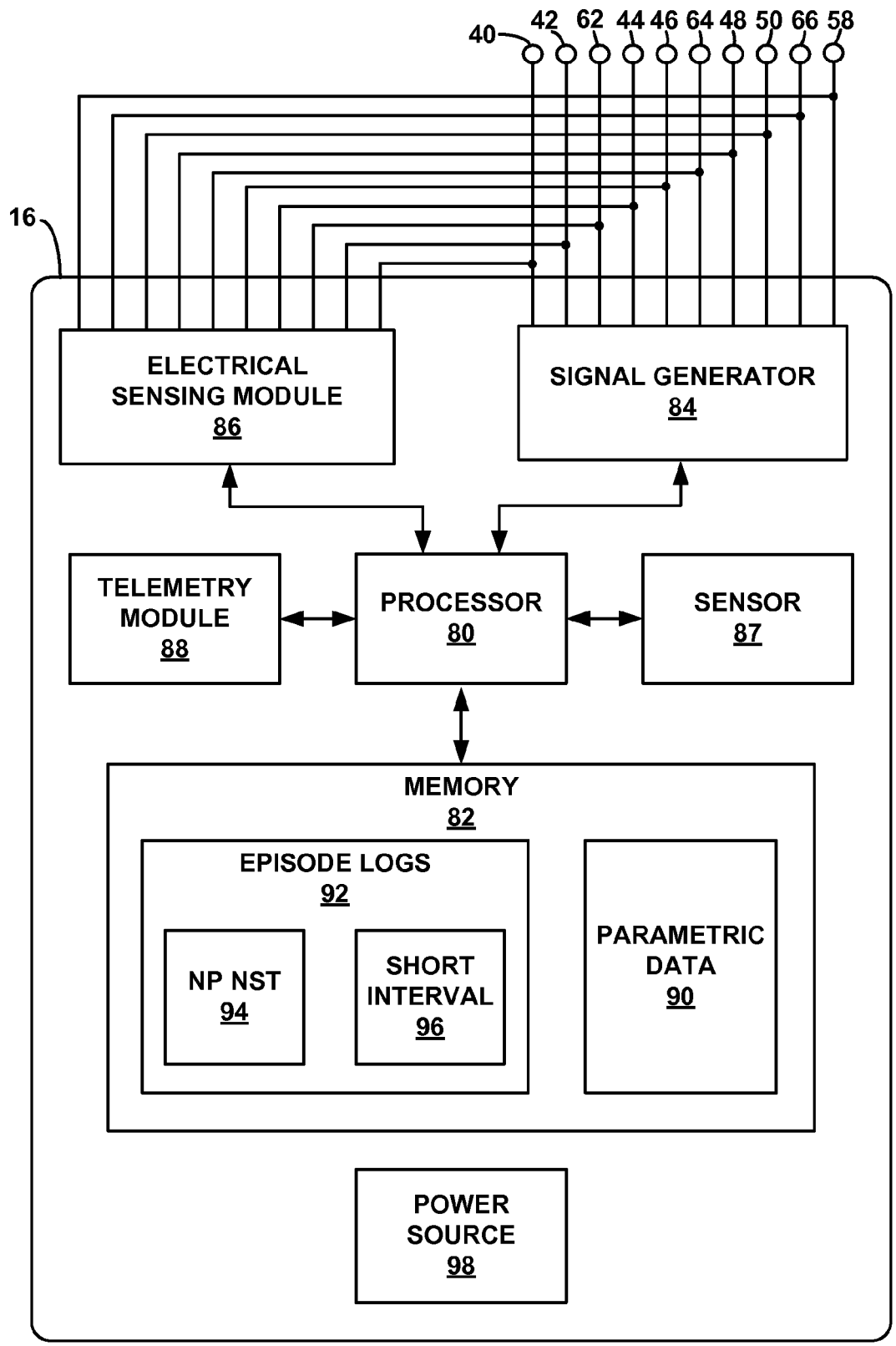
FIG. 4 is a functional block diagram illustrating an example configuration of the IMD of FIG. 1.

FIG. 4 is a functional block diagram illustrating one example configuration of IMD 16. In the example illustrated by FIG. 4, IMD 16 includes a processor 80, memory 82, signal generator 84, electrical sensing module 86, sensor 87, telemetry module 88, and power source 98. Memory 82 may includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12. Processor 80 may control signal generator 84 to deliver stimulation according to a selected one or more therapy programs, which may be stored in memory 82. For example, processor 80 may control signal generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver pacing, cardioversion, or defibrillation pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing electrode configuration, via the switch module within electrical sensing module 86, e.g., by providing signals via a data/address bus. Electrical sensing module 86 may include multiple detection channels, each of which may comprise an amplifier. In response to the signals from processor 80, the switch module of within electrical sensing module 86 may couple selected electrodes to each of the detection channels.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other components of processor 80, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals to electrical sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves with detection channels of electrical sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by signal generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as an atrial or ventricular fibrillation or tachycardia. Processor 80 may use the count in the interval counters to detect NSTs, suspected non-physiological NSTs, and short intervals based on R-R or P-P intervals, as will be described in greater detail below.

In some examples, processor 80 may operate as an interrupt driven device that is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998, or in U.S. patent application Ser. No. 10/755,185, filed Jan. 8, 2004 by Kevin T. Ousdigian, entitled "REDUCING INAPPROPRIATE DELIVERY OF THERAPY FOR SUSPECTED NON-LETHAL ARRHYTHMIAS." U.S. Pat. No. 5,545,186 to Olson et al., U.S. Pat. No. 5,755,736 to Gillberg et al., and U.S. patent application Ser. No. 10/755,185 by Kevin T. Ousdigian are incorporated herein by reference in their entireties. However, other arrhythmia detection methodologies may also be employed by processor 80 in other examples.

In the event that processor 80 detects an atrial or ventricular tachyarrhythmia based on signals from electrical sensing module 86, and an anti-tachyarrhythmia pacing regimen is desired, timing intervals for controlling the generation of anti-tachyarrhythmia pacing therapies by signal generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation pulses to heart 12, signal generator 84 may include a high voltage charge circuit and a high voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like the pacer timing and control module, be a hardware component of processor 80 and/or a firmware or software module executed by one or more hardware components of processor 80. The cardioversion/defibrillation control module may initiate charging of the high voltage capacitors of the high voltage charge circuit of signal generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by signal generator 84 is controlled by the cardioversion/defibrillation control module of processor 80. Following delivery of the fibrillation or tachycardia therapy, processor 80 may return signal generator 84 to a cardiac pacing function and await the next successive interrupt due to pacing or the occurrence of a sensed atrial or ventricular depolarization.

Signal generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of signal generator 84.

IMD 16 may comprise one or more sensors, such as sensor 87 illustrated in the example of FIG. 4. Sensor 87 may be within housing 60 (FIG. 2) of IMD 16. IMD 16 may additionally or alternatively be coupled to one or more sensors located outside of housing 60 of IMD 16. Sensor 87 may be located on or within on or more of leads 18, 20 and 22, or another lead which may or may not include stimulation/sensing electrodes. In some examples, sensor 87 may be separately housed from IMD 16, and may be coupled to IMD 16 via wireless communication. Sensor 87 may be implanted or external.

Sensor 87 may comprise, as examples, a pressure sensor, a motion sensor, a heart sound sensor, or any sensor capable of generating a signal that varies a function of mechanical activity, e.g., contraction, of heart 12. A pressure sensor may be, for example, a capacitive pressure sensor that senses an intracardiac or other cardiovascular pressure. A motion sensor may be, for example, an accelerometer or piezoelectric element. Processor 80 may receive one or more signals from sensor 87 or a plurality of sensors. Processor 80 may monitor, among other things, the mechanical activity of heart 12 based on such signals.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus.

In some examples, processor 80 may transmit atrial and ventricular heart signals (e.g., EGM signals) produced by atrial and ventricular sense amp circuits within electrical sensing module 86 to programmer 24. Programmer 24 may interrogate IMD 16 to receive the EGMs. Processor 80 may store EGMs within memory 82, and retrieve stored EGMs from memory 82. Processor 80 may also generate and store marker codes indicative of different cardiac events that electrical sensing module 86 detects, such as ventricular and atrial depolarizations, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Processor 80 may store cardiac EGMs for physiological episodes, such as tachyarrhythmias, within episode logs 92 in memory 82. For example, processor 80 may store cardiac EGMs for atrial and ventricular tachycardia and fibrillation episodes, in response to the detection of the tachycardia or fibrillation using any of the techniques described above. Processor 80 may also store cardiac EGMs for NSTs within episode logs 92, in response to detection of the NSTs using any of the techniques described above.

In some examples according to this disclosure, processor 80 identifies suspected non-physiological NSTs, and stores EGMs for the suspected non-physiological (NP) NSTs 94 within episode logs 92. Processor 80 may identify a suspected non-physiological NST based on, for example, the rate of sensed cardiac events, e.g., depolarizations, detected by electrical sensing module 86 during the NST. A cardiac event rate above a threshold may be more likely the result of a sensing integrity condition, e.g., sensing module 86 misidentifying noise as depolarizations, than an actual tachyarrhythmia.

In some examples, processor 80 additionally or alternatively identifies a suspected non-physiological NST based on a morphological analysis of signals received from electrical sensing module 86 during the NST, which may distinguish between noise and cardiac depolarizations. For example, a morphological analysis may include any one or more of an amplitude regularity analysis, an analysis of the width of the QRS complex or other features of the EGM, or an analysis of slew rates. In some examples, a morphological analysis may involve a wavelet analysis, such as those described in U.S. Pat. No. 6,393,316, entitled "METHOD AND APPARATUS FOR DETECTION AND TREATMENT OF CARDIAC ARRHTHMIAS," which issued to Gillberg et al. on May 21, 2002, and U.S. Pat. No. 7,176,747, entitled "IDENTIFICATION OF OVERSENSING USING SINUS R-WAVE TEMPLATE," which issued to Gunderson et al. on Jan. 23, 2007. In some examples, the analysis may include the far-field EGM analysis techniques described in U.S. Pat. No. 7,333,855 to Gunderson et al., entitled "METHOD AND APPARATUS FOR DETERMINING OVERSENSING IN A MEDICAL DEVICE," which issued on Feb. 19, 2008. The entire content of each of U.S. Pat. Nos. 6,393,316, 7,176,747 and 7,333,855 is incorporated herein by reference in its entirety.

In some examples, a processor 80 additionally or alternatively identifies a suspected non-physiological NST based on the presence or absence of a confirmatory indication of tachyarrhythmia from one or more other sensing channels or sensors 87. Another sensing channel may include a different sensing electrode configuration than the primary sensing electrode configuration used by electrical sensing module 86 to detect a cardiac signal during the suspected non-physiological? NST, and/or different signal processing circuitry, e.g., a different channel or amplifier, of sensing module 86. Processor 80 may detect mechanical activity (e.g., contraction) of heart 12 based on the signals provided by one or more sensors 87, and processor 80 may determine whether cardiac depolarizations detected by electrical sensing module 86 are correlated with mechanical activity of the heart to determine whether an NST is suspected of being non-physiological.

In some examples, processor 80 determines whether to store EGMs for suspected non-physiological episodes or events based on satisfaction of an impedance integrity criterion. The impedance integrity criterion may be satisfied based on one or more impedance measurements of one or more electrical paths. Each electrical path includes a plurality of electrodes (e.g., electrodes 40, 42, 44, 46, 48, 50, 58, 62, 64 or 66. An electrical path for which impedance is measured may include the electrodes used to sense cardiac electrical signals. In some examples, processor 80 may store EGMs for detected short intervals 96 if the impedance integrity criterion has been met. A short interval may be an interval between consecutive cardiac depolarizations detected by electrical sensing module 86 that is less than a threshold. An interval shorter than the threshold may indicate a sensing integrity condition, e.g., the device or system misidentifying noise as a depolarization for one or both of the sensed depolarizations. Thus, processor 80 may detect short intervals by determining an interval between consecutive cardiac events detected by electrical sensing module 86, e.g., based on the values within counters maintained by processor 80 when reset by detection of a depolarization by the sensing module.

Processor 80 may store marker channel data for each EGM, including EGMs 94 and 96, within the episode logs 92 in association with the EGMs. As illustrated in FIG. 4, processor 80 may also store parametric data 90 within memory 82. Parametric data 90 may include, for example, impedance measurements, trends of impedance measurements, or statistical or other processed values determined based on impedance measurements. Parametric data 90 may include an indication of whether an impedance integrity criterion has been satisfied, and data resulting in satisfaction of the criterion. Parametric data 90 may also include other sensing integrity data, such as counts of suspected non-physiological NSTs and short intervals, and indications of whether a sensing integrity criterion is satisfied. Processor 80 may provide parametric data 90 to programmer 24 or other external devices via telemetry module 88. A clinician may review parametric data 90 in conjunction with suspected non-physiological NST episode logs 94 and short interval episode logs 96 for identification of sensing integrity conditions.

The various components of IMD 16 are coupled to power source 98, which may include a rechargeable or non-rechargeable battery. A non-rechargeable battery may be capable of holding a charge for several years, while a rechargeable battery may be inductively charged from an external device, e.g., on a daily or weekly basis.

Figure 5:
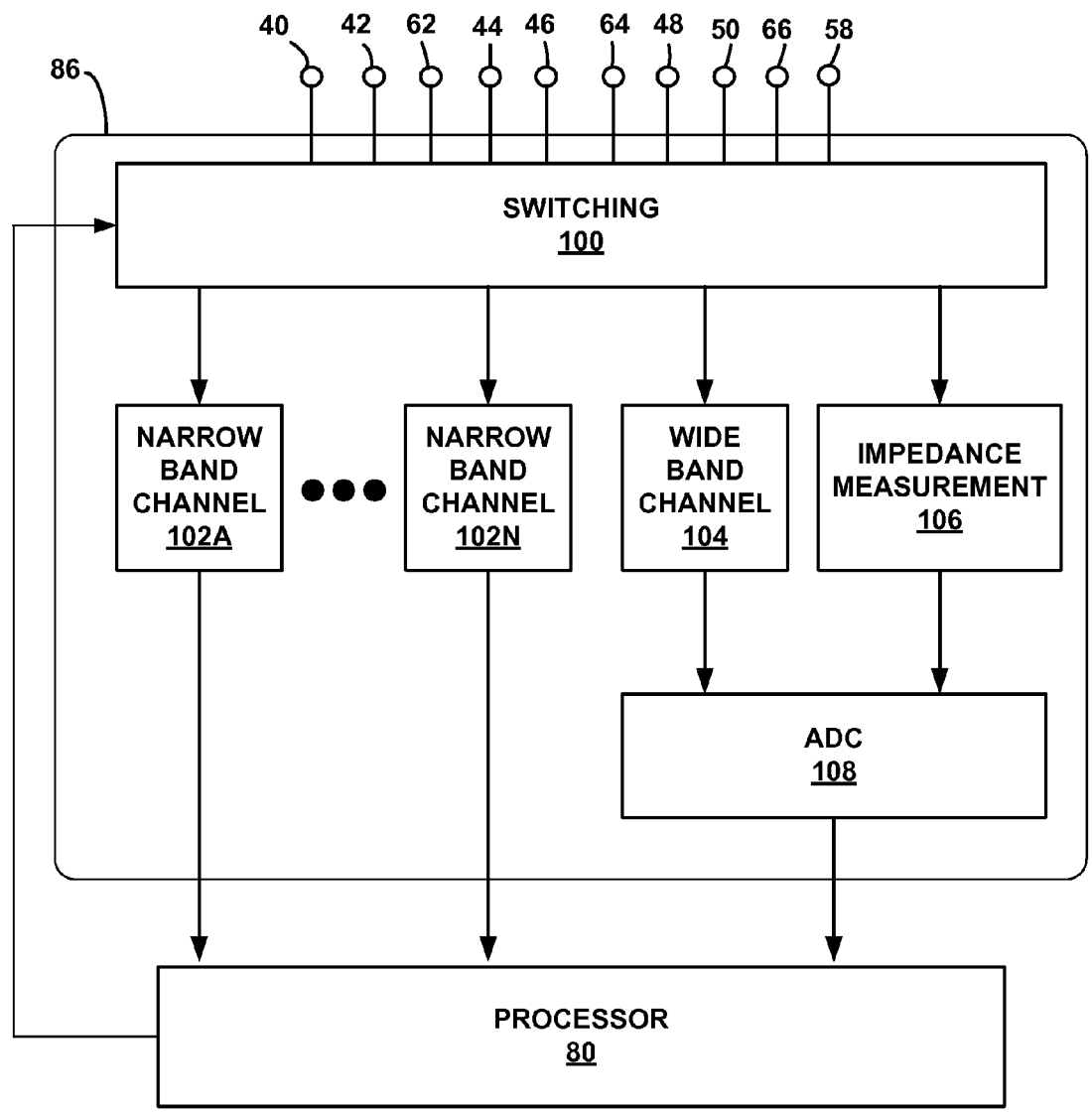
FIG. 5 is a functional block diagram illustrating an example electrical sensing module of the IMD of FIG. 1.

FIG. 5 is a block diagram of an example configuration of electrical sensing module 86. As shown in FIG. 5, electrical sensing module 86 includes multiple components including a switching module 100, narrow band channels 102A to 102N (collectively "narrow band channels 102"), wide band channel 104, impedance measurement module 106, and analog to digital converter (ADC) 108. Switching module 100 may, based on control signals from processor 80, control which of electrodes 40, 42, 44, 46, 48, 50, 58, 62, 64 and 66 is coupled to which of channels 102 and 104 and impedance measurement module 106, at any given time.

Each of narrow band channels 102 may comprise a narrow band filtered sense-amplifier that compares the detected signal to a threshold. If the filtered and amplified signal is greater than the threshold, the narrow band channel indicates that a certain electrical heart event has occurred. Processor 80 then uses that detection in measuring frequencies of the detected events. Narrow band channels 102 may have distinct functions. For example, some various narrow band channels may be used to detect either atrial or ventricular events.

In one example, at least one narrow band channel 102 may include an R-wave amplifier that receives signals from the sensing electrode configuration of electrodes 40 and 42, which are used for sensing and/or pacing in right ventricle 28 of heart 12. Another narrow band channel 102 may include another R-wave amplifier that receives signals from the sensing electrode configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel 102 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

Wide band channel 104 may comprise an amplifier with a relatively wider pass band than the R-wave or P-wave amplifiers. Signals from the sensing electrode configuration that is selected for coupling to this wide-band amplifier may be converted to multi-bit digital signals by ADC 108. In some examples, processor 80 may store signals the digitized versions of signals from wide band channel 104 in memory 82 as EGMs. In some examples, the storage of such EGMs in memory 82 may be under the control of a direct memory access circuit.

In some examples, processor 80 may employ digital signal analysis techniques to characterize the digitized signals from wide band channel 104 to, for example detect and classify the patient's heart rhythm. Processor 80 may detect and classify the patient's heart rhythm by employing any of the numerous signal processing methodologies known in the art. Further, in some examples, processor 80 may analyze the morphology of the digitized signals from wide band channel 104 to distinguish between noise and cardiac depolarizations. Based on such morphological analysis, processor may detect a suspected non-physiological NST.

In some examples, sensing module 86 and/or processor 80 are capable of collecting, measuring, and/or calculating impedance data for any of a variety of electrical paths that include two or more of electrodes 40, 42, 44, 46, 48, 50, 58, 62, 64 and 66. In such examples, impedance measurement module 106 may measure electrical parameter values during delivery of an electrical signal between at least two of the electrodes. Processor 80 may control signal generator 84 to deliver the electrical signal between the electrodes. Processor 80 may determine impedance values based on parameter values measured by impedance measurement module 106. In particular, ADC 108 may digitize parameter values measured by impedance measurement module 106, and processor 80 may determine impedance values based on the digitized parameter values and store the impedance values as parametric data 90 in memory 82.

In some examples, processor 80 may perform an impedance measurement by controlling delivery, from signal generator 84, of a voltage pulse between first and second electrodes. Impedance measurement module 106 may measure a resulting current, and processor 80 may calculate a resistance based upon the voltage amplitude of the pulse and the measured amplitude of the resulting current as digitized by ADC 108. In other examples, processor 80 may perform an impedance measurement by controlling delivery, from signal generator 84, of a current pulse between first and second electrodes. Impedance measurement module 106 may measure a resulting voltage, and processor 80 may calculate a resistance based upon the current amplitude of the pulse and the measured amplitude of the resulting voltage as digitized by ADC 108. Impedance measurement module 106 may include circuitry for measuring amplitudes of resulting currents or voltages, such as sample and hold circuitry.

In these examples of performing impedance measurements, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may collect impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components. Impedance data may include actual, measured impedance values, or may include values that can be used to calculate impedance (such as current and/or voltage values).

In one embodiment, processor 80 may analyze the measured impedance values, and may compare these values, or other computed values, to determined thresholds and identify any possible conditions with one or more electrical paths that include two or more of the electrodes. For example, processor 80 may, as a result of one or more comparisons, determine that one or more of leads 18, 20, and 22 has a lead-related condition, or more specifically that one or more electrodes or associated conductors within the leads may have an integrity condition. Processor 80 may send impedance measurement and/or analysis data to programmer 24 via telemetry module 88.

Figure 6:
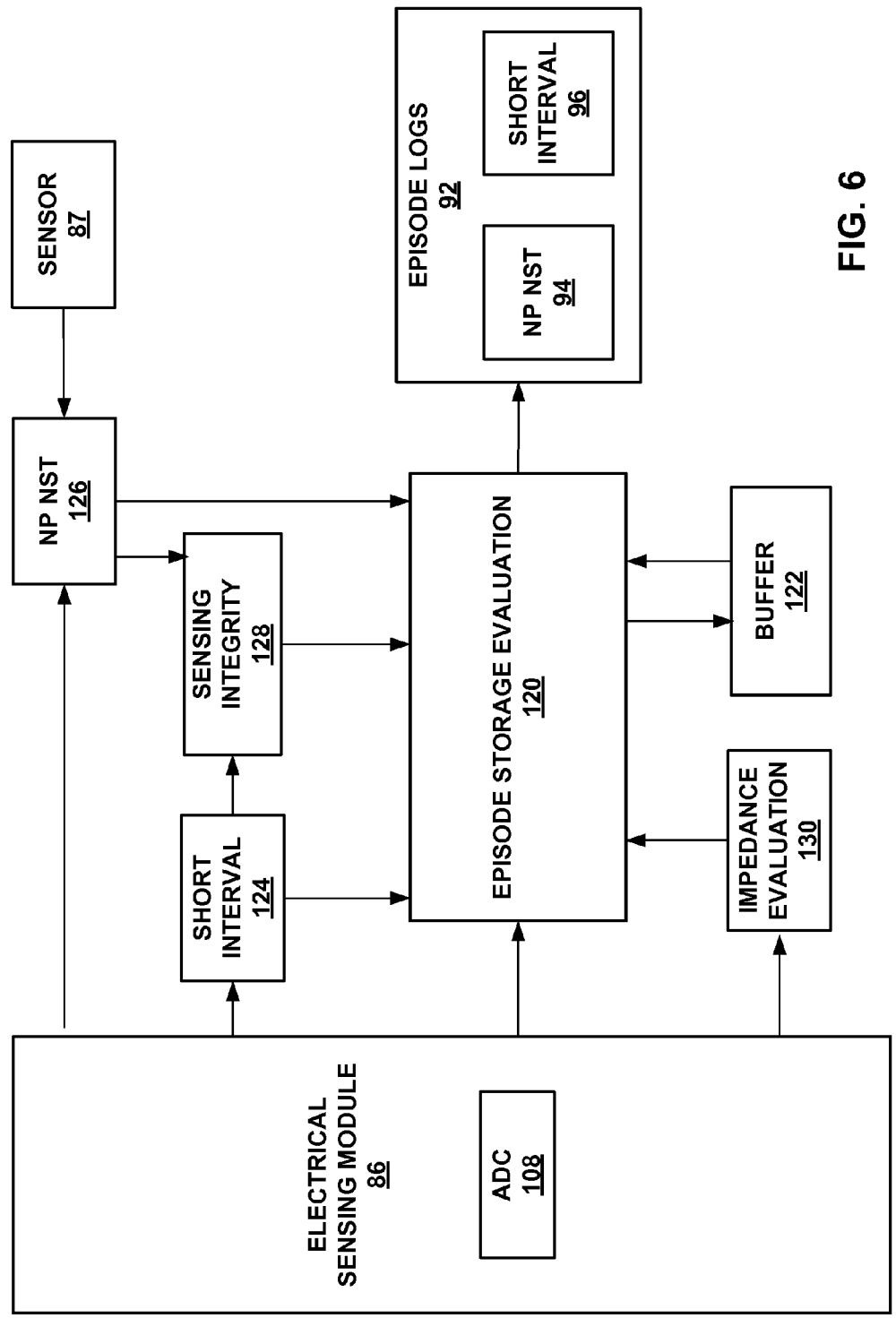
FIG. 6 is a functional block diagram illustrating an example episode storage evaluation module that determines whether to store an electrogram (EGM) for an episode and other associated modules.

FIG. 6 is a functional block diagram illustrating an episode storage evaluation module 120 that determines whether to store an EGM for an episode in conjunction with other associated modules. As illustrated by FIG. 6, episode storage evaluation module 120 may determine whether to store a digitized signal from ADC 108 of electrical sensing module 86 as a non-physiological NST EGM 94 or short interval EGM 96 within episode logs 92 of memory 82. Episode storage evaluation module 120 may also determine whether to buffer the digitized signal from ADC 108 within buffer 122 to provide EGM data prior to detection of a non-physiological NST or short interval.

These determinations by episode storage evaluation module 120 may be informed, in various examples, by input from a short interval detection module 124, a suspected non-physiological NST detection module 126, a sensing integrity module 128, or an impedance evaluation module 130. Any or all of modules 120, 124, 126, 128 and 130 may be implemented as software or firmware modules executing on processor 80. Modules 120, 124, 126, 128 and 130 may be implemented one or more hardware components of IMD 16, and some or all of modules may be implemented in devices other than IMD 16. Buffer 122 may be provided within memory 82 of IMD 16, or another memory, which may be located within another device.

Short interval detector 124 may detect short intervals by comparing the interval between consecutive cardiac events detected by sensing module 86, such as depolarizations, to a threshold. An example threshold is 200 milliseconds (ms), although other thresholds are contemplated.

Suspected non-physiological NST detector 126 detects non-physiological NSTs based on the rate of cardiac events sensed by sensing module 86. For example, non-physiological NST detector 126 may determine whether a threshold number of consecutive sensed cardiac events, e.g., at least five consecutive events, meet one or more criteria for detecting tachyarrhythmias, such as a tachycardia detection criterion or a fibrillation detection criterion. These criteria may be based on the rate of the sensed cardiac events.

Furthermore, suspected non-physiological NST detector 126 may compare the rate of the sensed cardiac events to another threshold to determine whether the NST is suspected of being non-physiological. For example, non-physiological NST detector 126 may compare an average of intervals between consecutive events, e.g., four depolarizations, to a threshold, such as 220 ms. The numbers of events, rates, and interval values are examples, and other examples are contemplated. In some examples, non-physiological NST detector 126 may additionally or alternatively detect a suspected non-physiological NST based on a comparison of the rate of events detected by electrical sensing module 86 via a primary sensing electrode configuration to a rate of events detected via a secondary sensing electrode configuration, based on a morphological analysis of a digitized EGM signal received from ADC 108, or based on a comparison of detected cardiac events, e.g., the rate of detected cardiac events, to mechanical activity of heart 12 as indicated by sensor 87.

Sensing integrity evaluation module 128 may determine whether sensing integrity condition criteria are satisfied based on one or both of short intervals detected by short interval detector 124 and suspected non-physiological NSTs detected by non-physiological NST detector 126. For example, sensing integrity evaluation module 128 may determine that the sensing integrity condition criteria are satisfied when there has been a threshold number of suspected non-physiological NSTs during a first predetermined period, and threshold number of short intervals during a second predetermined period. An example is two suspected non-physiological NSTs within the past sixty days and thirty short intervals within three days, e.g., any three of the sixty days. Other examples are contemplated.

Impedance evaluation module 130 may determine whether an impedance integrity criterion is satisfied. For example, impedance evaluation module 130 may compare impedance measurements derived from the measured electrical parameters received from sensing module 86 and ADC 108 to one or more thresholds to determine whether an impedance integrity criterion is satisfied.

Further details regarding example techniques for detecting short intervals and non-physiological NSTs, as well as determining whether impedance and other sensing integrity criteria are satisfied, may be found in U.S. Pat. No. 7,289,851 to Gunderson et al., entitled "METHOD AND APPARATUS FOR IDENTIFYING LEAD-RELATED CONDITIONS USING IMPEDANCE TRENDS AND OVERSENSING CRITERIA," which issued on Oct. 30, 2007, as well as U.S. Provisional Application No. 61/058,153 by Stadler et al., entitled "IMPEDANCE VARIABILITY ANALYSIS TO IDENTIFY LEAD-RELATED CONDITIONS," which was filed on Jun. 2, 2008. Both U.S. Pat. No. 7,289,851 and U.S. Provisional Application No. 61/058,153 are incorporated herein by reference in their entirety.

Episode storage evaluation module 120 may store an EGM for a suspected non-physiological NST 94 within an episode log based on detection of a suspected non-physiological NST by module 126. Episode storage evaluation module 120 may also determine whether to store an EGM for a suspected non-physiological episode, such as an NST, or event based on whether impedance evaluation module 130 has determined that an impedance integrity criterion has been satisfied. For example, episode storage evaluation module 120 may store an EGM for a detected short interval 96 if short interval detection module 124 indicates detection of a short interval and impedance evaluation module 130 indicates that the impedance integrity criteria has been met. As another example, episode storage evaluation module 120 may store an EGM for an non-physiological NST 96 if non-physiological NST detection module 126 indicates detection of an non-physiological NST and impedance evaluation module 130 indicates that the impedance integrity criteria has been met.

Episode storage evaluation module 120 may suspend storage of EGMs for short intervals 96 when a suspected non-physiological NST is detected by non-physiological NST detector 126. An EGM for a suspected non-physiological NST may be more probative of sensing integrity conditions than an EGM for a short interval. Episode storage evaluation module 120 may suspend storage of EGMs for short intervals when a suspected non-physiological NST is detected to conserve memory resources and ensure that EGMs for suspected non-physiological NSTs are retained in the memory.

In some examples, episode storage evaluation module 120 may only store EGMs for short intervals 96 if a sensing integrity criterion involving detection of non-physiological NSTs has not been previously satisfied. In this manner, episode storage evaluation module 120 may avoid overwriting EGMs for non-physiological NSTs 94 with possibly less probative EGMs for short intervals 96. Episode storage evaluation module 120 may, in some examples, overwrite EGMs for non-physiological NSTs 94 with EGMs for new non-physiological NSTs 94.

In some examples, episode storage evaluation module 120 may buffer EGM data in buffer 122 to enable storing a period of the EGM that preceded detection of a suspected non-physiological NST or short interval. However, buffering EGM data may consume memory or other resources of IMD 16. In some examples, episode storage evaluation module 120 determines whether to buffer EGM data based on indications from modules 128 and 130 as to whether an impedance integrity criteria or other sensing integrity criteria has been met. In other words, episode storage evaluation module 120 may begin buffering EGM data when impedance integrity criteria or other sensing integrity criterion has been met.

Figure 7:
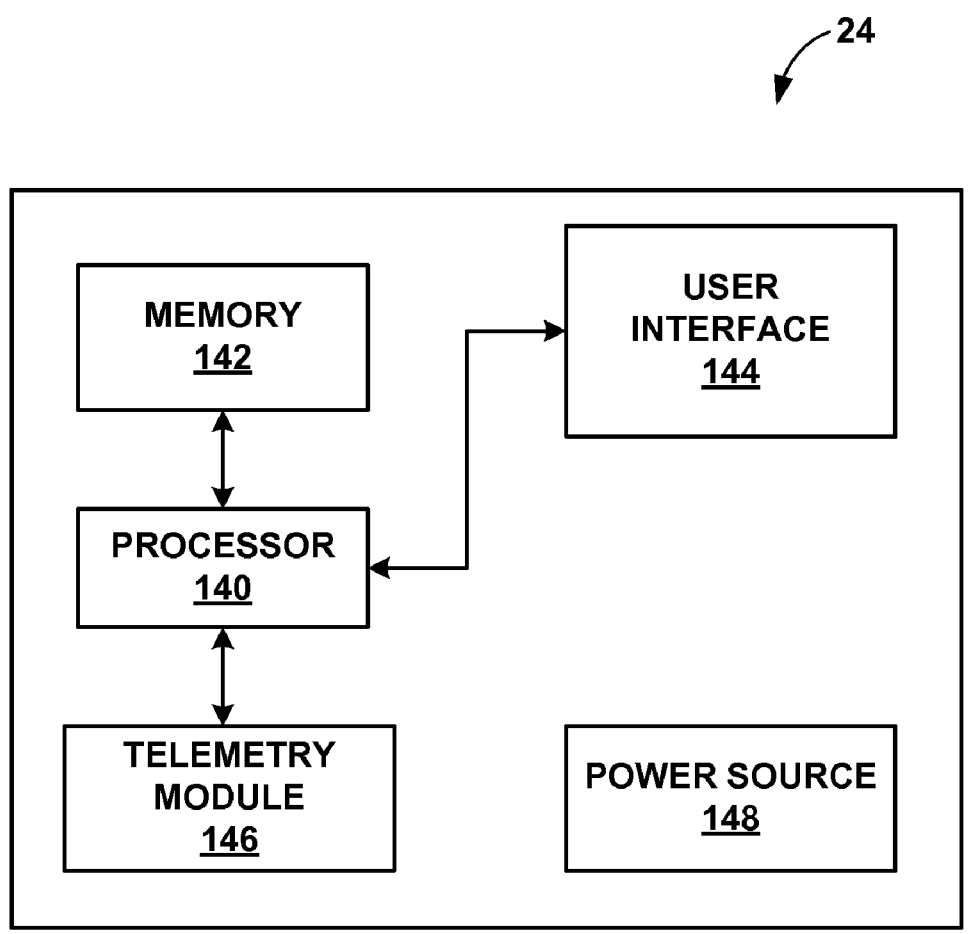
FIG. 7 is a functional block diagram of an example configuration of the external programmer shown in FIG. 1, which facilitates user communication with an IMD.

FIG. 7 is block diagram of an example programmer 24. As shown in FIG. 7, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 144 which may include display to present graphical user interface to a user, and a keypad or another mechanism for receiving input from a user.

Processor 140 can take the form one or more microprocessors, DSPs, ASICs, FPGAs, programmable logic circuitry, or the like, and the functions attributed to processor 140 herein may be embodied as hardware, firmware, software or any combination thereof. Processor 140 of programmer 24 may implement any of the modules depicted in FIG. 6, provide any of the functionality ascribed herein to processor 80 of IMD 16, or otherwise perform any of the methods described herein.

Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 4).

Telemetry module 142 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Power source 148 delivers operating power to the components of programmer 24. Power source 148 may include a battery and a power generation circuit to produce the operating power. In some embodiments, the battery may be rechargeable to allow extended operation. Recharging may be accomplished by electrically coupling power source 148 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 144 may include circuitry to monitor power remaining within a battery. In this manner, user interface 144 may provide a current battery level indicator or low battery level indicator when the battery needs to be replaced or recharged. In some cases, power source 148 may be capable of estimating the remaining time of operation using the current battery.

Figure 8:
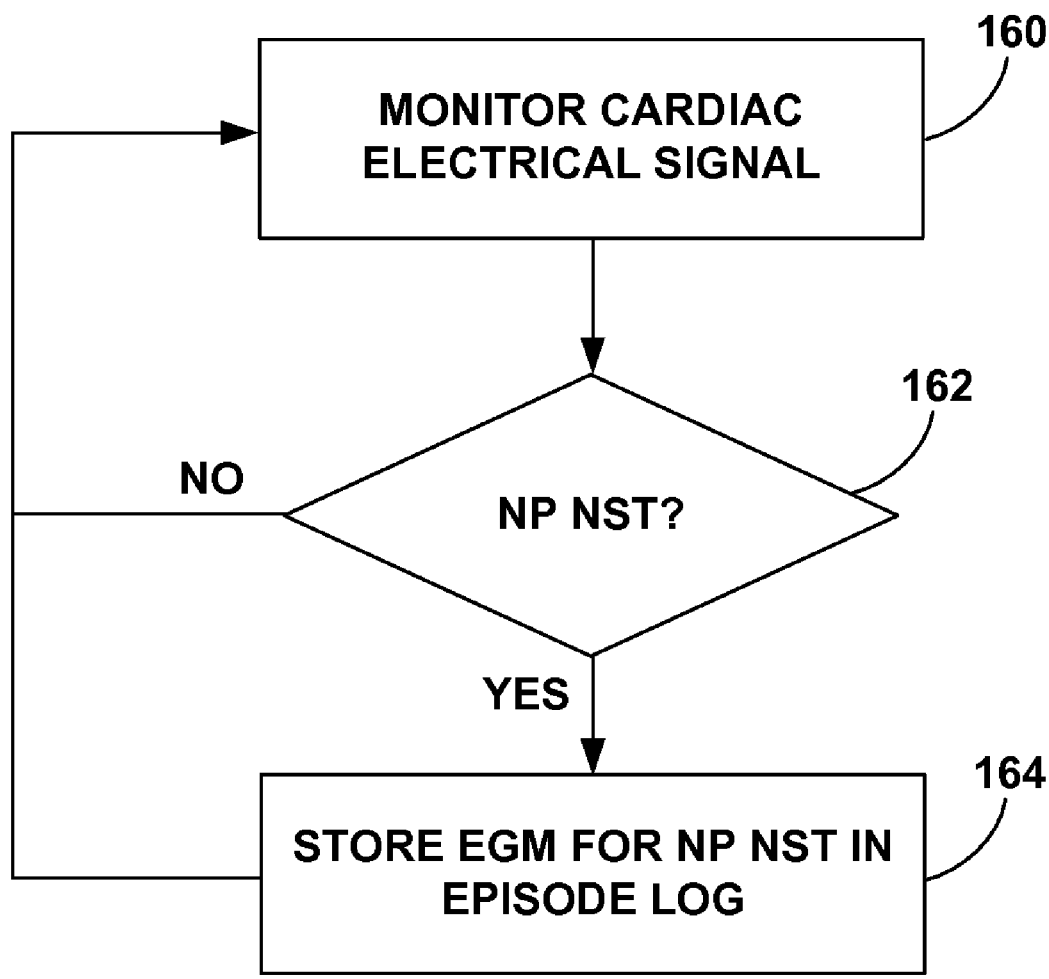
FIG. 8 is a flow diagram illustrating an example method for storing EGMs for non-sustained tachyarrhythmias (NSTs).

FIG. 8 is a flow diagram illustrating an example method for storing EGMs for suspected non-physiological non-sustained tachyarrhythmias (NP NSTs). Although described as being performed by processor 80 of IMD 16, the example method may be performed by any processor or module described herein, or combination thereof.

According to the example method, processor 80 monitors a cardiac electrical signal (160). For example, electrical sensing module 86 may receive a signal from a sensing electrode configuration coupled to the sensing module, and detect cardiac events based on the signal. Processor 80 may receive indications of the cardiac events from electrical sensing module 86.

Processor 80 also monitors for the occurrence of a suspected NP NST based on the monitored signal (162). For example, processor 80 may detect a suspected NP NST based on the rate of cardiac events detected by electrical sensing module 86, as described above. In some examples, as described above, processor 80 may additionally or alternatively detect an NP NST based on a comparison of the rate of events detected by electrical sensing module 86 via a primary sensing electrode configuration to a rate of events detected by electrical sensing module 86 via a secondary sensing electrode configuration, based on a morphological analysis of a digitized EGM signal received from ADC 108, or based on a comparison of detected cardiac events, e.g., the rate of detected cardiac events, to mechanical activity of heart 12 as indicated by sensor 87. If processor 80 detects an NP NST, processor 80 stores an EGM for the NP NST 94 as an episode log 92 within memory 82 of IMD 16 (164).

Figure 9:
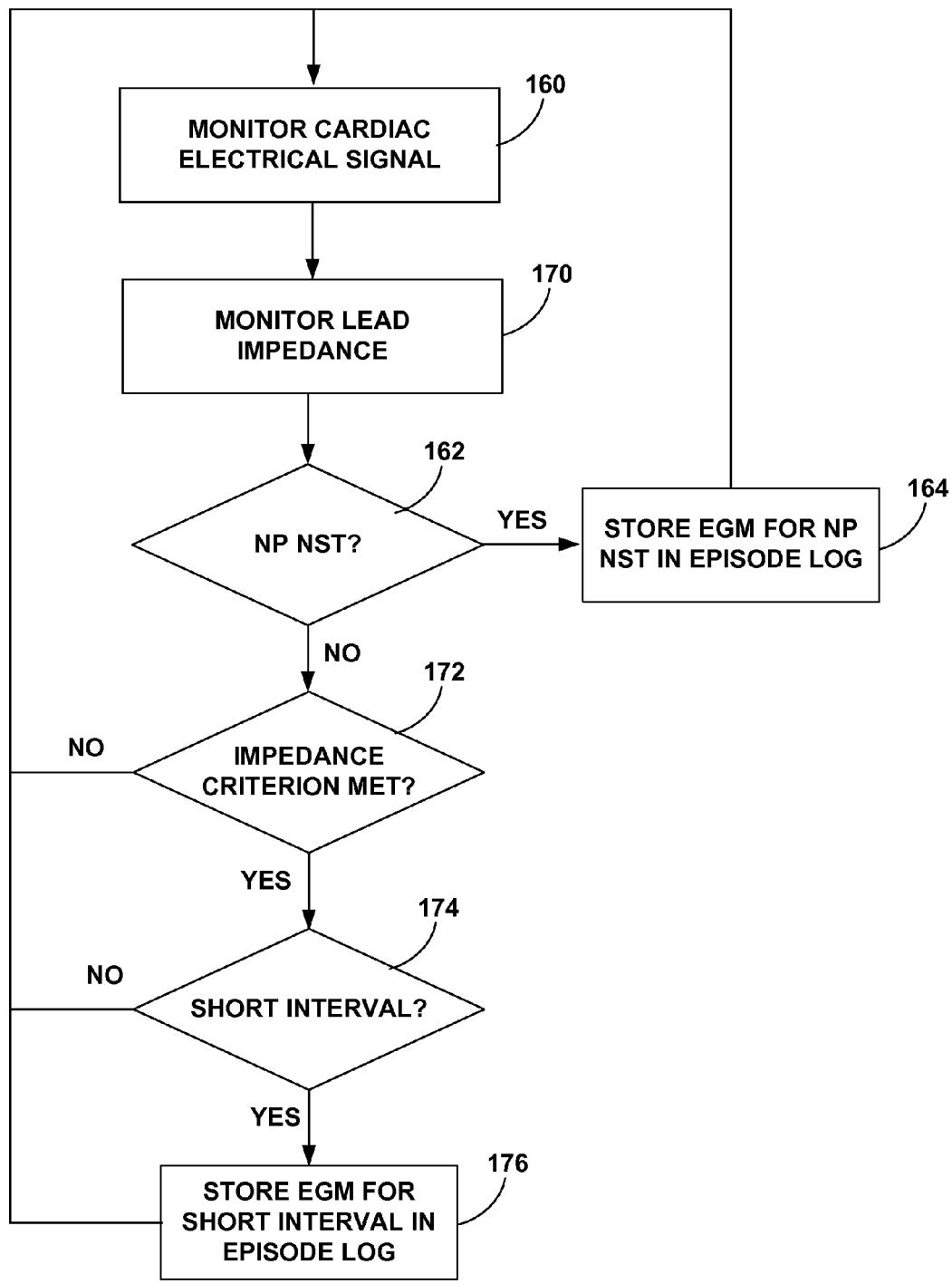
FIG. 9 is a flow diagram illustrating an example method for storing EGMs for NSTs and short intervals.

FIG. 9 is a flow diagram illustrating an example method for storing EGMs for suspected non-sustained tachyarrhythmias (NSTs) and short intervals. The example method of FIG. 9 is described as being performed by episode storage evaluation module 120 and the related modules of FIG. 6. As described above, these modules may be implemented by any one or more of the processors described herein, including processor 80 of IMD 16. The example method of FIG. 9 may be performed by any one or more processors or devices described herein.

According to the example method, electrical sensing module 86 monitors a cardiac electrical signal, and makes one or more lead impedance measurements over time (160, 170). NP NST detector 126 monitors for a suspected NP NST based on the monitored cardiac signal and, in some cases, signals generated by other sensors 87, as described above (162). For example, NP NST detector 126 may receive indications of cardiac events detected by electrical sensing module 86, and detect a suspected NP NST based on a rate of the cardiac events.

If NP NST detector 126 has not detected a suspected NP NST, episode storage evaluation module 120 determines whether an impedance criterion has been met based on an indication from impedance monitoring module 130 (172). If the impedance criterion has been met, episode storage module 120 determines whether short interval detector 124 has detected a short interval (174). If short interval detector 124 detects a short interval, episode storage evaluation module 120 stores an EGM for the short interval 96 as an episode log 92, e.g., within memory 82 of IMD 16 (176). Episode storage evaluation module 120 or another module may store a marker channel with the EGM for the short interval 96 as part of the episode log 92. In some examples, episode storage evaluation module 120 only monitors for indications of short intervals from short interval detector 124 when impedance monitoring module 130 indicates that the impedance criterion has been met. In other words, in some examples, episode storage evaluation module 120 only stores EGMs for short intervals if the impedance criterion has been met. As discussed above, in some examples episode storage evaluation module 120 may only store EGMs for short intervals 96 if a sensing integrity criterion involving detection of non-physiological NSTs has not been previously satisfied.

If episode storage evaluation module 120 determines that a suspected NP NST has been detected based on an indication from NP NST detector 126 (162), episode storage evaluation module 120 stores an EGM for the suspected NP NST 94 as an episode log 92, e.g., within memory 82 of IMD 16 (164). In some examples, episode storage evaluation module 120 does not monitor for indications of short intervals from short interval detector 124 after NP NST detector 126 indicates that a suspected NP NST has been detected. In other words, in some examples, episode storage evaluation module 120 only stores EGMs for short intervals so long as the impedance criterion has been met and no suspected NP NSTs have been detected. As previously described, this may help conserve memory resources of IMD 16 and ensure that EGMs for suspected non-physiological NSTs are retained in memory 82.

Furthermore, although episode storage evaluation module 120 is described with respect to FIG. 9 as storing an EGM for any suspected NP NST, in some examples the storage of EGMs for NP suspected NSTs may be limited in a manner similar to the storage of EGMs for short intervals. For example, episode storage evaluation module 120 may only monitor for indications of suspected NP NSTs from NP NST detector 126 when impedance monitoring module 130 indicates that the impedance criterion has been met. In other words, in some examples, episode storage evaluation module 120 only stores EGMs for suspected NP NSTs if the impedance criterion has been met.

Figure 10:
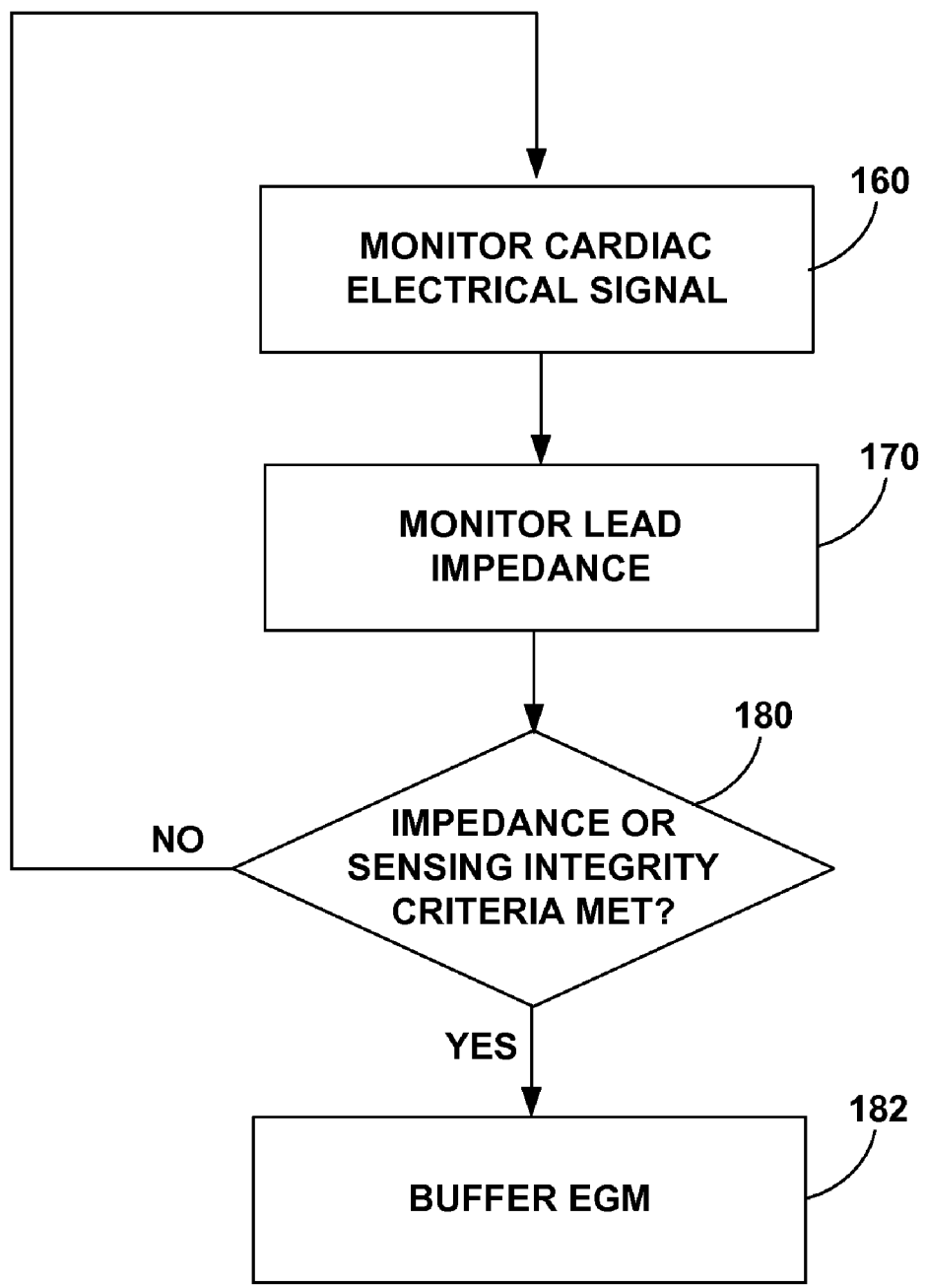
FIG. 10 is a flow diagram illustrating an example method for determining whether to buffer EGM data.

FIG. 10 is a flow diagram illustrating an example method for determining whether to buffer EGM data. The example method of FIG. 9 is described as being performed by episode storage evaluation module 120 and the related modules of FIG. 6. As described above, these modules may be implemented by any one or more of the processors described herein, including processor 80 of IMD 16. The example method of FIG. 9 may be performed by any one or more processors or devices described herein.

According to the example method, electrical sensing module 86 monitors a cardiac electrical signal, and makes one or more lead impedance measurements over time (160, 170). Episode storage evaluation module 120 determines whether an impedance criterion and/or another sensing integrity criterion has been met based on indications received from sensing integrity module 128 and impedance evaluation module 130 (180). If either (or in some examples both) of the criteria are met, episode storage evaluation module 120 buffers EGM data within buffer 122 to, for example, enable inclusion of EGM data before a suspected NP NST or short interval within an episode log 92 for the suspected NP NST or short interval (182). Marker channel data may be similarly buffered.

Figure 11:
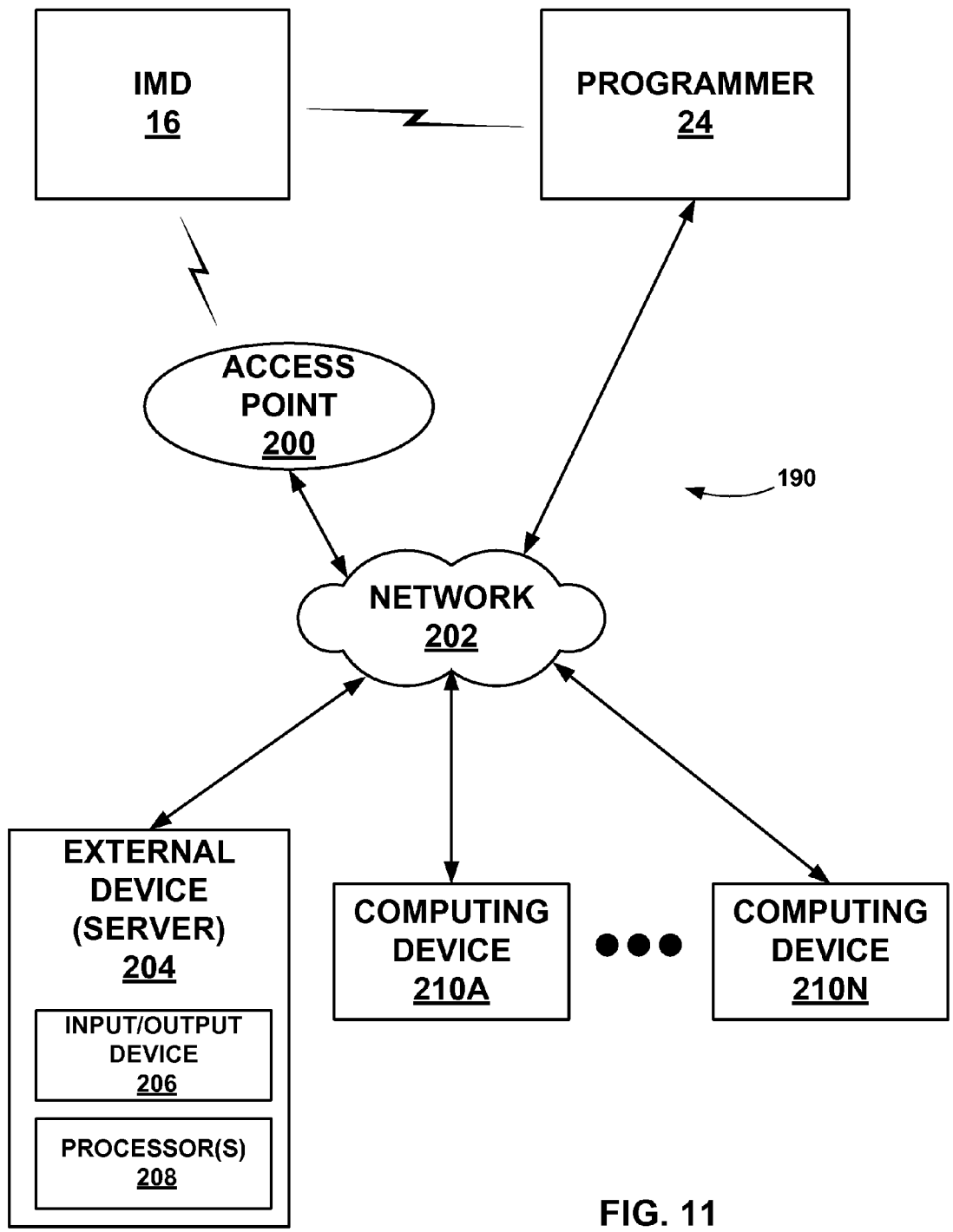
FIG. 11 is a block diagram illustrating an example system that includes an external device, such as a server, and one or more computing devices that are coupled to the IMD and programmer shown in FIG. 1 via a network.

FIG. 11 is a block diagram illustrating an example system 190 that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 11, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein. For example, as illustrated in FIG. 11, server 204 may comprise one or more processors 208 and an input/output device 206, which need not be co-located.

Server 204 may, for example, practice the methods described herein for determining whether to store an EGM (and in some cases a marker channel) for a suspected non-physiological episode or event. Server 204 may store EGMs (and in some cases a marker channels) within episode logs 92 maintained by server 204. Server 204 may implement any or all of the modules illustrated in FIG. 6. Furthermore, in some examples in which IMD 16 determines whether to store an EGM as described above, server 204 may provide a database or other memory for storing the EGMs (and in some cases a marker channels). IMD 16 may store EGMs within an external storage unit or memory, which may be provided by server 204 as one example, or programmer 24 another.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some embodiments, server 204 or one or more of the computing devices 210A-210N may perform any of the various functions or operations described herein.

Network 202 may comprise a local area network, wide area network, or global network, such as the Internet. In some cases, programmer 24 or server 204 may assemble episode logs 92, including EGMs 94 and 96, and other sensing integrity information in web pages or other documents for viewing by and trained professionals, such as clinicians, via viewing terminals associated with computing devices 210A-210N.

System 190 may be implemented, in some aspects, with general network technology and functionality similar to that provided by the Medtronic CareLink® Network developed by Medtronic, Inc., of Minneapolis, Minn.

Although the disclosure is described with respect to cardiac stimulation therapy, such techniques may be applicable to other therapies in which sensing integrity is important, such as, e.g., spinal cord stimulation, deep brain stimulation, pelvic floor stimulation, gastric stimulation, occipital stimulation, functional electrical stimulation, and the like. In such therapies, the techniques described in this disclosure may be applied to evaluate sensing integrity and detect possible lead-related conditions.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   receiving a cardiac electrical signal and monitoring heart rate based on the cardiac electrical signal;
   detecting a tachyarrhythmia based on the monitored heart rate exceeding a first predetermined threshold;
   determining whether the detected tachyarrhythmia is a non-sustained tachyarrhythmia based on the length of the detected tachyarrhythmia episode;
   identifying a plurality of events in the cardiac electrical signal during the detected non-sustained tachyarrhythmia episode as cardiac depolarizations;
   determining a rate of at least some of the identified events;
   determining that the detected non-sustained tachyarrhythmia is a suspected non-physiological non-sustained tachyarrhythmia caused by a sensing integrity condition, based on the rate of the at least some of the identified events; and
   storing an electrogram for the suspected non-physiological non-sustained tachyarrhythmia based on the detection, the electrogram including at least a portion of the cardiac electrical signal.

2. The method of claim 1, further comprising storing a marker channel corresponding to the electrogram in association with the electrogram, wherein the marker channel indicates detection of cardiac events based on the cardiac electrical signal.

3. The method of claim 1, further comprising:
   monitoring an impedance of at least one electrical path comprising at least one electrode that senses the cardiac signal; and
   determining whether an impedance integrity criterion is met based on the monitored impedance,
   wherein storing an electrogram for the suspected non-physiological non-sustained tachyarrhythmia comprises storing the electrogram if the impedance integrity criterion is met.

4. The method of claim 1, further comprising:
   detecting a plurality of cardiac events based on the signal prior to detection of the suspected non-physiological non-sustained tachyarrhythmia;
   measuring one or more intervals between consecutive ones of the detected cardiac events;
   comparing the intervals to a threshold;
   identifying one or more short intervals based on the comparison, wherein the short intervals are intervals with lengths shorter than the threshold;
   storing an electrogram for each of the one or more short intervals, each of the one or more electrograms for the one or more short intervals including at least a portion of the cardiac electrical signal; and
   stopping storage of electrograms for the one or more short intervals in response to detection of the suspected non-physiological non-sustained tachyarrhythmia.

5. The method of claim 4, further comprising:
   monitoring an impedance of at least one electrical path comprising at least one electrode that senses the cardiac signal; and
   determining whether an impedance integrity criterion is met based on the monitored impedance,
   wherein storing one or more electrograms for the one or more short intervals comprises storing the electrograms if the impedance integrity criterion is met.

6. The method of claim 1, further comprising:
   determining whether a sensing integrity criterion is met; and
   buffering the cardiac electrical signal for storage of the electrogram if the sensing integrity criterion is met.

7. A system comprising:
   a memory;
   a plurality of electrodes;
   an electrical sensing module that receives a cardiac electrical signal from the plurality of electrodes and monitors heart rate based on the cardiac electrical signal;
   a non-physiological non-sustained tachyarrhythmia detection module configured to
   detect a tachyarrhythmia based on the monitored heart rate exceeding a first predetermined threshold determine whether the detected tachyarrhythmia is a non-sustained tachyarrhythmia based on the length of the detected tachyarrhythmia episode;

identify a plurality of events in the cardiac electrical signal during the detected non-sustained tachyarrhythmia episode as cardiac depolarizations;

determine a rate of at least some of the identified events; and determine that the detected non-sustained tachyarrhythmia is a suspected non-physiological non-sustained tachyarrhythmia caused by a sensing integrity condition, based on the rate of the at least some of the identified events; and an episode storage evaluation module that controls storage of an electrogram for the suspected non-physiological non-sustained tachyarrhythmia within the memory based on the detection, the electrogram including at least a portion of the cardiac electrical signal.

8. The system of claim 7, wherein the episode storage evaluation module controls storage of a marker channel corresponding to the electrogram in association with the electrogram, wherein the marker channel indicates detection of cardiac events based on the cardiac electrical signal.

9. The system of claim 7, further comprising an impedance integrity module that monitors an impedance of at least one electrical path comprising at least one of the electrodes, and determines whether an impedance integrity criterion is met based on the monitored impedance, wherein the episode storage evaluation module controls storage of the electrogram if the impedance integrity criteria is met.

10. The system of claim 7, wherein the electrical sensing module detects a plurality of cardiac events based on the signal prior to detection of the suspected non-physiological non-sustained tachyarrhythmia by the non-physiological non-sustained tachyarrhythmia detection module, the system further comprising a short interval detection module that measures one or more intervals between consecutive ones of the detected events, compares the intervals to a threshold, and identifies one or more short intervals based on the comparison, and wherein the episode storage evaluation module controls storage of an electrogram for each of the one or more short intervals, each of the one or more electrograms for the one or more short intervals including at least a portion of the cardiac electrical signal, and stops storage of electrograms for short intervals in response to detection of the suspected non-physiological non-sustained tachyarrhythmia by the non-physiological non-sustained tachyarrhythmia detection module.

11. The system of claim 10, further comprising an impedance integrity module that monitors an impedance of at least one electrical path comprising at least one of the electrodes, and determines whether an impedance integrity criterion is met based on the monitored impedance, wherein the episode storage evaluation module controls storage of the electrograms for the one or more short intervals if the impedance integrity criteria is met.

12. The system of claim 7, further comprising a sensing integrity module that determines whether a sensing integrity criterion is met, wherein the episode storage evaluation module buffers the cardiac electrical signal for storage of the electrogram if the sensing integrity criterion is met.

13. The system of claim 12, wherein the sensing integrity module comprises an impedance integrity module that monitors an impedance of at least one electrical path comprising at least one of the electrodes, and determines whether an impedance integrity criterion is met based on the monitored impedance.

14. The system of claim 7, further comprising an implantable medical device coupled to the electrodes and comprising the memory, the electrical sensing module, and a processor, wherein the processor comprises the non-physiological non-sustained tachyarrhythmia detection module and the episode storage evaluation module.

15. The system of 14, wherein the implantable medical device comprises at least one of a cardiac pacemaker, a cardioverter, or a defibrillator.

16. A system comprising:

means for receiving a cardiac electrical signal;

means for monitoring heart rate based on the cardiac signal;

means for detecting a tachyarrhythmia based on the monitored heart rate exceeding a first predetermined threshold;

means for determining whether the detected tachyarrhythmia is a non-sustained tachyarrhythmia based on the length of the detected tachyarrhythmia episode;

means for identifying a plurality of events in the cardiac electrical signal during the detected non-sustained tachyarrhythmia episode as cardiac depolarizations;

means for determining a rate of at least some of the identified events;

means for determining that the detected non-sustained tachyarrhythmia is a suspected non-physiological non-sustained tachyarrhythmia caused by a sensing integrity condition, based on the rate of the at least some of the identified events; and means for storing an electrogram for the suspected non-physiological non-sustained tachyarrhythmia based on the detection, the electrogram including at least a portion of the cardiac electrical signal.

17. A computer readable medium comprising instructions that cause a processor to:

detect a tachyarrhythmia based on a cardiac electrical signal and a monitored heart rate exceeding a first predetermined threshold;

detect a tachyarrhythmia based on the monitored heart rate exceeding a first predetermined threshold determine whether the detected tachyarrhythmia is a non-sustained tachyarrhythmia based on the length of the detected tachyarrhythmia episode;

identify a plurality of events in the cardiac electrical signal during the detected non-sustained tachyarrhythmia episode as cardiac depolarizations;

determine a rate of at least some of the identified events; and determine that the detected non-sustained tachyarrhythmia is a suspected non-physiological non-sustained tachyarrhythmia caused by a sensing integrity condition, based on the rate of the at least some of the identified events; and control storage of an electrogram for the suspected non-physiological non-sustained tachyarrhythmia based on the detection, the electrogram including at least a portion of the cardiac electrical signal.

18. A system comprising:

a memory;

a plurality of electrodes;

an electrical sensing module that receives a cardiac electrical signal from the plurality of electrodes and measures an impedance of an electrical path comprising the electrodes; and a processor that identifies a plurality of events within the cardiac electrical signal, compares an interval between two consecutive events to a threshold, and determines whether to store an electrogram for the interval within the memory based on the comparison and the impedance measurement, the electrogram including at least a portion of the cardiac electrical signal, wherein the processor detects a suspected non-physiological non-sustained tachyarrhythmia based on the cardiac electrical signal, and determines not to store the electrogram for the interval based on the detection of the non-physiological non-sustained tachyarrhythmia.

* * * * *